United States Patent [19]

Barnes

[11] Patent Number: 5,128,125
[45] Date of Patent: Jul. 7, 1992

[54] METHOD FOR PREPARING FINELY DIVIDED NYLON-4 COMPLEX WITH IODINE AND ANTISEPTIC PREPARATION MADE THEREFROM

[76] Inventor: Arthur C. Barnes, 178 Perry Ave., Norwalk, Conn. 06850

[21] Appl. No.: 596,570

[22] Filed: Oct. 11, 1990

Related U.S. Application Data

[63] Continuation of Ser. No. 156,160, Feb. 16, 1988, abandoned.

[51] Int. Cl.$^5$ ............... A61K 31/785; A61K 33/18
[52] U.S. Cl. ................ 424/78.08; 528/313; 528/319
[58] Field of Search ............ 528/319, 492, 313; 424/78, 78.08

[56] References Cited

U.S. PATENT DOCUMENTS

| | | | |
|---|---|---|---|
| 3,405,099 | 10/1968 | Taber | 528/319 |
| 3,890,280 | 6/1975 | Upadhyaya | 528/319 |
| 4,113,851 | 9/1978 | Leveen et al. | 424/78 |
| 4,247,683 | 1/1981 | Barnes et al. | 528/313 |

FOREIGN PATENT DOCUMENTS 2031441  4/1980  United Kingdom .

*Primary Examiner*—Thurman K. Page
*Assistant Examiner*—Peter F. Kulkosky
*Attorney, Agent, or Firm*—Davis Hoxie Faithfull & Hapgood

[57] ABSTRACT

Finely divided nylon-4 particles are prepared from a solution of polypyrrolidone in 2-pyrrolidone by precipitation in water. The washed particles are contacted with iodine to provide a water insoluble complex for use in biocidal pharmaceutical compositions which slowly release elemental iodine over time.

8 Claims, No Drawings

METHOD FOR PREPARING FINELY DIVIDED NYLON-4 COMPLEX WITH IODINE AND ANTISEPTIC PREPARATION MADE THEREFROM

This is a continuation of copending application Ser. No. 07/156,160 filed on Feb. 16, 1988, and now abandoned.

BACKGROUND OF THE INVENTION

1. Field of the Invention

This invention relates to the preparation of very finely divided particles, of polypyrrolidone (nylon-4), and to biocidal compositions containing iodine made from them, and specifically to the compound formed by complexing polypyrrolidone with iodine, the latter being broadly referred to as an iodophor.

2. The Prior Art

The complex of nylon-4 and iodine is disclosed in U.S. patent application Ser. No. 933,856 filed Aug. 15, 1978, which is a continuing application of Ser. No. 677,033 filed Apr. 4, 1977, which in turn was a continuing application of Ser. No. 525,845 filed Nov. 21, 1974, and in corresponding foreign patents, e.g., Canadian Patent No. 1,119,748. Among the uses described for this complex is that of an antiseptic and germicidal ointment for topical application where the sustained release of elemental iodine over a period of time will prevent infection of a wound or burn.

It has been suggested that particles prepared by grinding the solid polymer be employed in formulating the ointment. However, the solid polymer is very difficult to grind and conventional comminuting and grinding techniques produce a gritty material not completely suitable for use in ointments, that are intended for topical use on humans. Such powders are not sufficiently finely divided to disperse well in a matrix used for preparing ointments. Further, it is desirable that ointments be prepared from particles which are free of any gritty feel to the touch.

An antiseptic-germicidal ointment made from the iodine complex of polyvinylpyrrolidone, also known as PVP or povidone, has been sold as an over-the-counter preparation for many years. There is, however, an undesirable drawback when using this PVP complex. Polyvinylpyrrolidone is water soluble and accordingly its complex with iodine is water soluble. Because of this solubility the polymer complex can get into the blood stream and while the lower molecular weight components of this polymer may be eliminated by the kidney, the higher molecular weight material is retained and this build-up can cause kidney damage. It is possible to fractionate the polyvinylpyrrolidone used for making the iodine complex to at least partially eliminate the higher molecular weight material which is retained by the kidney. However, this process is not only expensive, but imperfect so that some high molecular weight material is still retained. In addition to the potential adverse physiological effects, the water soluble nature of the PVP iodine complex allows it to be diluted and washed away by perspiration as well as body fluids emanating from the wound, thereby leaving the site without biocidal protection. It is therefore desirable to provide an antiseptic ointment in which the iodine carrier is insoluble in water and therefore incapable of entering the blood stream, and which will not be washed away by exuded body fluids. The polypyrrolidone-iodine complex, unlike polyvinylpyrrolidone, is insoluble in water, as well as other common solvents, and its iodine complex is likewise insoluble.

The complex will form with polypyrrolidone in any physical form, e.g., molded objects, films, fibers, fibrils, particles, etc. For preparing an ointment a very fine particle size is required and heretofore it has not been possible to prepare such a fine material free from a gritty feel and readily dispersable.

The preparation of a complex of iodine with a water insoluble gel forming material for use as a disinfectant has been disclosed in U.S. Pat. No. 4,010,259 issued Mar. 1, 1977. The gel, or gel-forming hydrophilic organic compound is capable of complexing with iodine in an aqueous and/or ethanol solution to form an iodophor, from which iodine can be repeatedly extracted. This iodine carrier is prepared by reacting a polyhydoxyl organic compound, such as starch, polysaccharides or polyvinyl alcohol, with a so-called cross-linking agent that is a bi-functional glycerol derivative, such as epichlorohydrin. The iodophor obtained by this process is described as having utility in its dried particulate form in the preparation of ointments and powders for topical disinfectant use. However, the method of preparing the gel is relatively complex and requires numerous process steps which include prolonged heating, separation and the like, in order to obtain the iodophors.

In contrast, an excellent iodophor may be formed from polypyrrolidone in a few minutes as disclosed in the aforementioned patent application as well as in the issued foreign patents. The only obstacle to its use as an ointment for topical application is t he lack of a suitable non-gritty finely divided form of the polymer.

It is therefore an object of this invention to provide a novel and economical method of forming finely divided particles of polypyrrolidone which are readily dispensable.

It is likewise an object of this invention to provide a method of dispersing the finely divided nylon-4 particles without the formation of agglomerates.

It is also an object of this invention to produce finely divided particles of nylon-4 which are free of a gritty feel and smooth to the touch.

It is a further object of this invention to provide a commercially practical method of forming a relatively uniform, finely divided polymer of 2-pyrrolidone which has industrial utility as, for example, in cosmetic and pharmaceutical applications.

It is another object of this invention to provide a method of forming a complex of polypyrrolidone and iodine in a form suitable for making an ointment for topical application.

It is a still further object of this invention to provide finely divided and dispensable polypyrrolidone-iodine particles which are suitable for preparing iodophors in the form of ointments for human and veterinary use and which are insoluble in the blood stream and therefore cannot cause damage to the kidneys.

Other objects will be apparent from the more detailed description given below.

SUMMARY OF THE INVENTION

I have found that while polypyrrolidone is not soluble in its monomer to any appreciable extent at moderate temperatures, if the temperature of a mixture of monomer and solid polymer is raised to the range of 200°-220° C., complete dissolution of the polymer is obtained. The heating should be accomplished in as short a period of time as possible, and for this purpose a microwave oven is advantageously used.

To form a dispersable powder, the hot solution of polymer and monomer at about 200° C. is slowly poured into a container of hot water with agitation, such as a Waring blender set to operate at slow speed. The resulting milky liquid is then filtered in a fine fritted glass funnel. For larger quantities of material, a sintered metal filter of small pore size can be used. The filter cake is then washed with water to remove residual monomer or other solvent and it is then complexed with iodine by suspension in a $KI_3$ solution.

Upon an addition of the $KI_3$ solution the mixture develops a brown color as the complex is formed. After a period of stirring, the brown mixture is filtered leaving a brown filter cake. As the iodine content is increased, the color of the mixture darkens to a chocolate brown or black.

The filter cake is then removed and redispersed in water and the mixture again filtered to remove the excess $KI_3$. This process can be repeated until the excess $KI_3$ has been reduced to an acceptable level.

The normally dark chocolate brown filter cake is now ready for compounding to form an ointment. The cake cannot be dried further for, as with the uniodinated product, it will bond to itself.

A desired amount of the moist filter cake is combined with an ointment base such as petrolatum, lanolin, "Veegum" (colloidal magnesium aluminum silicate), glyceryl monostearate, polyethylene glycolmonostearate, etc. The moist iodinated filter cake readily disperses in the base with moderate stirring.

The pharmaceutical preparations containing the finely divided nylon-4 iodine complex of the invention are free of any gritty feel and exhibit sustained release of iodine when applied to the skin. Water based ointments may be removed by washing with water. Petrolatum or lanolin based ointments provide a more permanent means of maintaining iodine at the site since they are not removed by water or body fluids, but they may be removed with soap and water. In any case, the water insoluble polypyrrolidone-iodine complex cannot enter the blood stream.

DETAILED DESCRIPTION

Typically the invention is practiced by first preparing finely divided and dispersable polypyrrolidone by dissolving the polymer in its monomer, 2-pyrrolidone, and then precipitating it from the solution; the complex is prepared by contacting the finely divided polymer with a solution of $KI_3$.

EXAMPLE 1

140 grams of polypyrrolidone was mixed with 120 grams of 2-pyrrolidone in a 500 ml. flask. The mixture was placed in a microwave oven and heated at about 600 volts energy for 5 minutes to a temperature of about 200° C., after which time all the polymer had dissolved to form a colorless viscous solution. The mixture was not stirred during heating. The hot solution of polymer and monomer was poured into 100 ml. of warm water while stirring in a Waring blender at the slow speed setting. Following agitation for about one minute, the milky suspension was poured into a fritted glass funnel of fine pore size and the water removed by suction. The filter cake is pure white in color and is so firm that it can be removed in one piece if desired. The residual monomer was removed by washing once with water and then redispersing the filer cake in water. A magnetic stirrer is satisfactory for this purpose. The mixture was again filtered and the process repeated. The filter cake can not be dried further since nylon-4 readily bonds to itself as more water is removed resulting in the formation of lumps which cannot be redispersed. The cake must be used in the moist condition.

EXAMPLE 2

The white, well washed filter cake prepared in Example 1, weighing 171 grams, was redispersed in 400 ml water using a magnetic stirrer. To this mixture the $KI_3$ solution which had been prepared as follows, was slowly added while stirring:

$I_2$—16 grams
KI—32 grams
Water—70 ml

The color rapidly changed from a light tan upon the initial addition of $KI_3$, to a dark chocolate brown toward the end of the addition. After stirring for 15 minutes the mixture was filtered in the fritted glass funnel. The very dark chocolate brown filter cake was removed and redispersed in 400 ml of water and then filtered again. This process was repeated twice more in order to remove the excess $KI_3$. The mixture was filtered again to form an almost black filter cake which was removed, broken into several pieces and stored in a tightly capped bottle.

EXAMPLE 3

28 grams of the moist iodinated filter cake prepared in Example 2 was combined with 147 grams of petrolatum. The cake dispersed readily in the petrolatum to form an ointment having a very dark chocolate brown, almost black color. The ointment formed is not washed away by water or body fluids from a wound. Upon topical application it slowly releases iodine.

EXAMPLE 4

The procedure of Example 3 was followed except that 147 grams of lanolin was substituted for the petrolatum. The color of this ointment was not nearly as dark as that prepared with the petrolatum, being brown rather than chocolate brown. The ointment is not removed by water or exudate from a wound, but may be removed with soap and water.

EXAMPLE 5

The iodinated filter cake containing approximately 18% iodine was submitted to an independent laboratory for micro-biological testing. A Broth Dilution Susceptibility test, also known as a Minimum Inhibitory Concentration (MIC) test was carried out as well as a Minimum Bactericidal Concentration (MDC) test.

A suspension of 200 milligrams of the nylon-4 iodine complex per milliliter of Trypticase-soy broth was prepared and serially diluted to a concentration of 1.5 mg/ml in one milliliter volumes in $12 \times 75$ mm sterile tubes with Tripticase-soy broth. Four series were prepared each consisting of eight tubes with varying concentrations of the complex and a growth control tube containing only Tripticase-soy broth. Eight of the tubes in each series were then individually inoculated with approximately $2.5 \times 10^4$ organisms of the following four strains of bacteria: *Klebsiella pneumoniae, Proteus mirabilis, Pseudomonas aeruginosa* and *Staphylococcus aureus.*

All tubes were incubated at 35° C. for 18 hours. Growth of the bacteria as evidenced by turbidity or lack of turbidity at each concentration as compared to the turbidity of the growth control resulted in the MIC values reported below in Table 1.

Following incubation, approximately 0.01 ml of broth from each tube was subcultured onto plates of Trypticase-soy agar with 5% sheep blood. These plates were incubated for 18 hours at 35° C. The lowest concentration of the complex showing no subsequent growth was deemed to be the MBC. The results are reported under the heading MBC in Table 1. Cultures from each of the growth control tubes exhibited uninhibited growth.

TABLE 1

| Organism | MIC | MBC |
| --- | --- | --- |
| Klebsiella Pneumoniae | 6.25 mg/ml | 12.5 mg/ml |
| Proteus Mirabilis | 6.25 mg/ml | 12.5 mg/ml |
| Pseudomonas Aeruginosa | 25.0 mg/ml | 50.0 mg/ml |
| Staphylococcus Aureus | 12.5 mg/ml | 50.0 mg/ml |

These results indicate that the nylon-4 iodine complex exhibits biocidal activity against the organisms tested and only a three-fold dilution difference exists between the more resistant bacteria (*Pseudomonas aeruginosa* and *Staphylococcus aureus*) and the less resistant bacteria (*Klebsiella pneumoniae* and *Proteus mirabilis*) in this study.

As previously noted, the iodine complex prepared in accordance with this invention falls into the broad category of iodophors. As will be apparent to those skilled in the art, other iodophor-containing compositions having utility as biocides, antiseptics and the like can be prepared employing the methods falling within the scope of the invention.

Although I prefer to use monomeric 2-pyrrolidone as the solvent, other suitable liquid solvents can be employed. For example, N-methyl 2-pyrrolidone or 5-methyl 2-pyrrolidone may be substituted for the 2-pyrrolidone and the same procedure followed. Likewise, other lactams or amides having suitable melting points, such as e-caprolactam, formamide, acetamide and the like may also be used as a solvent. Preferably the solvent selected should be water soluble for easy removal.

I claim:

1. In the method of preparing finely divided particles of polypyrrolidone, the improvement which comprises the steps of
   (a) adding solid polypyrrolidone polymer to a solvent selected from the group consisting of 2-pyrrolidone monomer, N-methyl 2-pyrrolidone, 5-methyl 2-pyrrolidone formamide and acetamide;
   (b) heating the mixture of polymer and solvent to a sufficient temperature until the polymer is dissolved in the solvent;
   (c) mixing the hot solution of dissolved polymer and solvent with water to obtain a solid suspension of the polymer in water;
   (d) filtering the aqueous mixture to recover the solid polymer in the form of finely divided particles; and
   (e) washing the solid polymer to remove solvent.

2. The method of claim 1 where the solvent is 2-pyrrolidone monomer.

3. The method of claim 2 where the mixture of polymer and monomer is heated to about 200° C.

4. The method of claim 1 where the polymer and monomer are heated by microwave energy.

5. A method of preparing a complex of polypyrrolidone and iodine in a finely divided particulate form suitable for use in pharmaceutical compositions which comprises the steps of:
   (a) adding solid polypyrrolidone polymer to 2-pyrrolidone monomer;
   (b) rapidly heating the mixture of polymer and monomer until the polymer is dissolved in the monomer;
   (c) mixing the hot solution of dissolved polymer and monomer with water to obtain a solid suspension of the polymer in water;
   (d) filtering the aqueous mixture to recover the solid polymer in the form of finely divided particles;
   (e) washing the solid polymer to remove monomer;
   (f) contacting the particles with a solution of iodine and an iodide dissolved in a solvent in which the polypyrrolidone is insoluble for a time sufficient to permit formation of the polypyrrolidone-iodine complex; and
   (g) washing the solid particles to remove excess uncomplexed triiodide ions.

6. The method of claim 5 in which the solution of iodine and iodide is aqueous.

7. The method of claim 5 in which the complex is washed with water.

8. The method of claim 6 which includes the further step of partially drying the solid complex obtained to produce a water moistened powder.

* * * * *